United States Patent [19]

Czernecki et al.

[11] Patent Number: 5,124,442
[45] Date of Patent: Jun. 23, 1992

[54] PROCESS FOR PREPARING AZT (3'-AZIDO-3'-DEOXY-THYMIDINE) AND RELATED COMPOUNDS

[75] Inventors: Stanislas Czernecki, Maincy; Jean-Marc Valery, Nandy, both of France

[73] Assignee: Universite Pierre et Marie Curie (Paris VI), Paris, France

[21] Appl. No.: 603,010

[22] Filed: Oct. 25, 1990

[30] Foreign Application Priority Data

Oct. 27, 1989 [FR] France .................. 89 14132

[51] Int. Cl.$^5$ .......................................... C07H 17/00
[52] U.S. Cl. ............................................ 536/23
[58] Field of Search ......................... 536/23, 24

[56] References Cited

U.S. PATENT DOCUMENTS 4,681,933  7/1987  Chu et al. .................. 536/23

FOREIGN PATENT DOCUMENTS 199451  10/1986  European Pat. Off. .
253537   7/1989  European Pat. Off. .
WO88/05657  8/1988  PCT Int'l Appl. .

OTHER PUBLICATIONS

Hayauchi et al., CA 109-211404s (1988).
Yamamoto et al., J. C. S. Perkin I, p. 306 (1980).
Glinski et al., Journal of Organic Chemistry, 38, 4299 (1973).
Colla et al., European Journal Med. Chem.-Chim. Ther., 20, 295 (1985).
Lin et al., Journal of Medicinal Chemistry, 26, 544 (1983).
Loibner et al., Justus Liebigs Annalen Der Chemie, 78 (1978).
Kimura et al., Bulletin of the Chemical Society of Japan, 52, 1191 (1979).
Chemical Abstracts, No. 12166X, vol. 88, 590 (1978).

*Primary Examiner*—Cecilia Shen
*Attorney, Agent, or Firm*—Finnegan, Henderson, Farabow, Garrett and Dunner

[57] ABSTRACT

The present invention relates to a process for preparing a compound of formula I

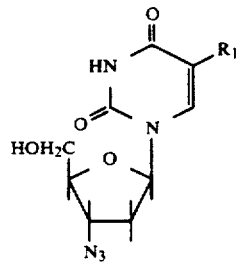

from a compound of formula II

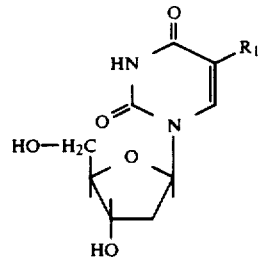

via a compound of formula IV

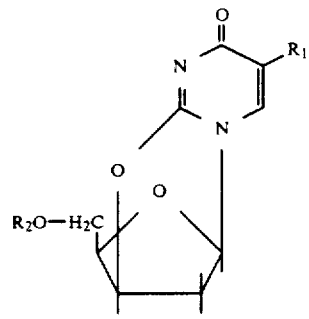

and to a compound of formula IV by way of an intermediate in the preparation of a compound of formula I.

17 Claims, No Drawings

PROCESS FOR PREPARING AZT (3'-AZIDO-3'-DEOXY-THYMIDINE) AND RELATED COMPOUNDS

The present invention relates to a process for the synthesis of 1-(3-azido-2,3-dideoxy-β-D-erythropentofuranosyl)thymine, also known as 3'-azido-3'-deoxythymidine or AZT, and of related compounds possessing antiviral properties and used, in particular, in combatting AIDS.

Various syntheses of AZT have been described. The most direct are carried out from thymidine, but comprise a fairly large number of steps and give, in the majority of cases, low yields.

However, two processes of synthesis have been described which comprise only three steps.

Thus, the paper published in 1984 (V.E. ZAITSEVA et al., Bioorg. Khim., 10, 670 (1984)) describes a synthesis of this type but which does not appear to have been developed, no doubt on account of the fact that the second step of the process necessitates the preparation of lithium p-methylbenzoate, and that the isolation of the AZT obtained in the final step is carried out by column chromatography.

A German Patent DE 3,705,794 A1 of Y. HAYAUCHI and O. LOCKHOFF, published in 1988, also describes this type of three-step process which yields AZT from thymidine, but in a yield of only 42.5%.

This process necessitates, moreover, the use of silicon-containing reagents and tetraalkylammonium fluoride, both of which are expensive compounds.

The subject of the present invention is a three-step process for preparing AZT and related compounds, but which possesses the advantages of being able to be carried out in only two successive reaction media, of employing inexpensive reagents and of leading readily to AZT or to the desired analogue in a satisfactory state of purity.

More especially, the present invention relates to a process for preparing a compound of formula (I)

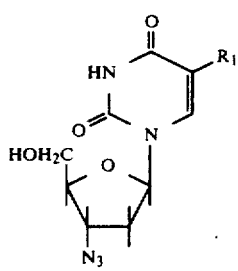

in which: $R_1$ is H, an alkyl radical or an alkoxy, hydroxyalkyl or halogen radical, from a compound of formula (II)

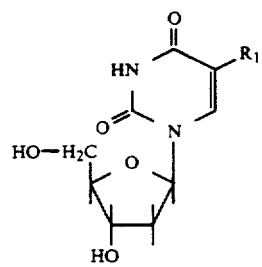

characterized in that the compound of formula II is reacted with a derivative $R_2X$ in which X represents a halogen, $R_2$ a trityl radical, a ($C_{1-3}$ mono- or dialkoxy)-trityl radical, a pixyl radical or a radical of the type $(R_3R_4R_5)Si$ where $R_3$, $R_4$ and $R_5$, independently of one another, represent an alkyl group having 1 to 5 carbon atoms or an aryl group, so as to obtain a compound of formula III

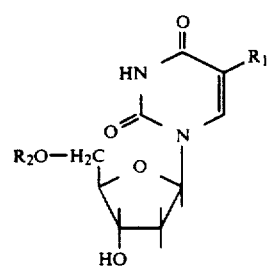

which is then converted, through the action of an azodicarboxylic acid diester and a phosphine or phosphite derivative in a solvent compatible with the reaction conditions, to form a compound of formula IV

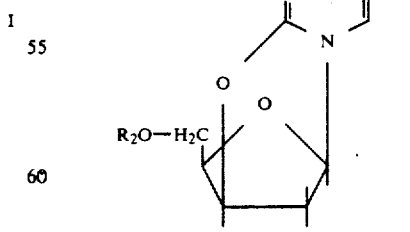

which, after an optional separation, is opened in the presence of a metal azide in a solvent compatible with the reaction conditions to lead to a compound of formula V

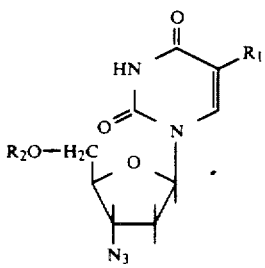

which, on deprotection of the 5' function, gives the compound of formula I.

Naturally, among the compounds are formula (I), AZT, that is to say the compound in which $R_1$ is equal to $CH_3$, should be mentioned more especially; nevertheless, at the present time, other 3'-azido derivatives are being developed, especially those in which $R_1$ is equal to a lower alkyl radical or a lower alkoxy or lower hydroxyalkyl radical containing from 1 to 5 carbon atoms, for example methyl or ethyl radicals.

Among these other derivatives, 3'-azido-3'-deoxyuridine may also be mentioned.

In the process according to the present invention, the starting material, especially for preparing AZT, is thymidine, a compound which is industrially available and which must, for the requirements of the process, be dehydrated since the presence of water considerably impairs the yield of the process.

Among reagents of the type $R_2X$, trityl chloride, an inexpensive and readily available compound, will preferably be chosen.

Another important feature of the process lies in the fact that it is unnecessary to purify or isolate the compound (III) thereby obtained, provided that conditions compatible with the preparation of the 2,3'-anhydro compound of formula (IV) are used.

The present invention also relates to this compound of formula (IV) by way of a synthesis intermediate for the preparation of a compound of formula (I).

Such conditions consist, for example, in combining an anhydrous aprotic solvent and a sufficiently strong organic or inorganic base.

Among solvents, DMF, HMPT and DMSO should be mentioned. On the grounds of cost, DMF is the preferred solvent, on account of the fact that it makes it possible both to prepare the compound of formula IV directly, and also to carry out the opening of the latter without having to isolate it.

Among organic bases, tertiary amines such as 4-dimethylaminopyridine (DMAP), 1,4-diazabicyclo[4.3.0]-non-5-ene (DBN), 1,4-diazabicyclo[2.2.2]octane (DABCO), 1,8-diazabicyclo[5.4.0]undec-7-ene (DBU) and triethyl- or tri-n-butylamine should be mentioned.

Among inorganic bases, alkali metal carbonates are suitable.

The production of the compound of formula (IV) results from the action, under conditions such as those which are defined above, of an azodicarboxylic acid diester $R_6O—OC—N=N—CO—OR_6$ in the presence of a phosphine or phosphite derivative.

Among the latter, the preferred phosphine is triphenylphosphine, which is readily accessible industrially.

Similarly, the azodicarboxylic acid diesters can be aryl or lower alkyl esters ($R_7$, is equal to an alkyl group containing from 1 to 4 carbon atoms). However, the preferred products will be diisopropyl azodicarboxylate (DIAD) or diethyl azodicarboxylate (DEAD), since they are both readily accessible.

These various reagents are preferably used in molar excess relative to the compound of formula (III).

For this reaction, the temperature and pressure conditions are not, strictly speaking, characteristic. In effect, the reaction is complete after a few hours at room temperature. However, it may be further prolonged without incurring any problem.

At the end of this stage of the process, the compound of formula (IV) is obtained, which compound can either be treated without any prior separation, as will be described below, or be separated from the reaction mixture.

In this case, the separation is carried out by simple filtration, either after the addition of a dissolving intermediary such as diethyl ether, diisopropyl ether or n-butyl acetate which causes the total precipitation of the compound of formula (IV), or by using a small volume of solvent and/or a low temperature during the separation The compound of formula (IV) thereby obtained has the advantage of possessing good solubility, thereby facilitating the implementation of the following step.

The following reaction, which is the opening reaction, is performed by means of an excess of azide in a polar solvent. This excess can range from 1.5 to 15 equivalents per mole of compound of formula (IV). Alkali metal azides may be used. It is possible, in some cases, to limit the excess of reagent by carrying out the reaction in the presence of another lithium salt.

The solvent used is, in general, a polar aprotic solvent compatible with the reaction, that is to say enabling both the compound of formula (IV) and the azide used to be solubilized.

For this reason, this reaction will be performed, for example, in DMF or in a solvent which is a higher homologue, in the heated state, that is to say at temperatures of the order of 100° C. up to the refluxing temperature, which temperatures must remain compatible with the stability of the products involved.

The reaction will then be complete in a few hours, namely approximately 7 to 10 hours.

The separation of the compound of formula (V) formed at the end of this step may be performed by treating the reaction mixture with an alkali metal hydrogen carbonate and then by extracting with a halogenated solvent such as chloroform.

The organic phase is then washed with water, dried and evaporated in order to obtain a homogeneous product. This compound is then deprotected and thereafter extracted.

It is naturally possible to deprotect the compound of formula (V) directly from the reaction medium leading to this compound.

This deprotection is performed using an acidic reagent of the Lewis acid type, such as boron trifluoride etherate, or protic acid type such as, for example, halogen hydracids and/or acetic acid in the presence of water.

The removal of the various organic by-products is carried out simply by treating the crude reaction mixture with an aqueous alkaline base and then extracting with ether.

Neutralization of the resulting aqueous phase by means of a suitable acid then enables the compound of formula (I), especially AZT, to be recovered almost quantitatively.

The examples given below, without implied limitation, will enable other advantages and features of the present invention to be demonstrated.

EXAMPLE 1

4.95 g of thymidine and 6.83 g of trityl chloride in 60 ml of pyridine are heated to 110° C. for 1 hour 30 minutes. TLC (eluent: ethyl acetate) shows that the reaction is complete.

The reaction mixture is then poured slowly into 200 g of ice and 200 ml of water with brisk stirring. After 30 minutes, the white precipitate formed is drained, washed with cold water (50 ml) and dried. 7.4 g of III (75.5%) are obtained.

M.p. 128°-130° C.

|  | Elemental analysis | | |
|---|---|---|---|
|  | C | H | N |
| Calculated | 71.88% | 5.82% | 5.78% |
| Found | 71.83% | 5.85% | 5.71% |

EXAMPLE 2

4.85 g of III and 3.93 g of triphenylphosphine are dissolved in 50 ml of DMF. 2.95 ml of DIAD are added dropwise. The reaction is slightly exothermic and may be cooled with a waterbath.

After 30 minutes, TLC (eluents: ethyl acetate and chloroform/methanol, 6:1) shows that no starting material remains. The reaction medium is then poured into 500 ml of ether and stirred for 1 hour at 0° C. The precipitate obtained is drained, washed three times with 20 ml of ether and dried.

3.78 g of IV (81%) are obtained.
M.p. 152° C.
NMR and IR analyses confirm the structure of the compound IV.

|  | Elemental analysis | | |
|---|---|---|---|
|  | C | H | N |
| Calculated | 74.66% | 5.62% | 6% |
| Found | 74.66% | 5.59% | 5.95% |

EXAMPLE 3

335 mg of trityl chloride and 127 mg of sodium carbonate are added successively to a solution of 242 mg of thymidine in 3 ml of DMF.

After 5 hours at 110° C., the reaction mixture is allowed to return to room temperature and 393 mg of triphenylphosphine are added. After dissolution, 0.3 ml of DIAD is introduced.

The reaction is complete in a few hours and the reaction mixture is treated as in Example 2.

300 mg of IV (64%) are obtained.

EXAMPLE 4

940 mg of IV and 265 mg of sodium azide in 5 ml of DMF are heated to 140° C. for 6 hours.

The reaction mixture is poured into saturated sodium hydrogen carbonate solution (20 ml) and extracted with chloroform (3 × 15 ml).

After washing with water, drying and evaporation of the solvent, 1.08 g of V, homogeneous in TLC (eluent: ethyl acetate), are obtained.

The NMR spectrum shows the presence of approximately 5% of DMF.

The reaction is hence quantitative.

EXAMPLE 5

4.6 g of IV and 1.3 g of sodium azide in 25 ml of DMF are heated to 140° C. for 7 hours.

A treatment similar to that of Example 4 yields a syrup, which is dissolved in 30 ml of 80% strength acetic acid. After heating for 15 minutes to 120° C., TLC shows that deprotection is complete.

The mixture is cooled to 5° C. and treated with 145 ml of 3M sodium hydroxide (the pH must be equal to at least 9), and the resulting mixture is extracted with ether (2 × 40 ml).

The resulting aqueous phase is-neutralized with approximately 5M hydrochloric acid and then evaporated.

The crystalline mass obtained is taken up with 120 ml of hot ethyl acetate. The insoluble matter is filtered off while hot and washed with 20 ml of boiling ethyl acetate.

After cooling, the filtrate is diluted with an equivalent volume of methanol and treated with active charcoal. Filtration on Celite followed by evaporation of the solvents yields 2.45 g of the compound I (93%), homogeneous in TLC (eluent: ethyl acetate/methanol, 20:1) in the vitreous state.

Crystallization in water yields 1.92 g (73% based on IV) of AZT.

M.p. 117°-119° C.

We claim:

1. Process for preparing a compound of formula (I)

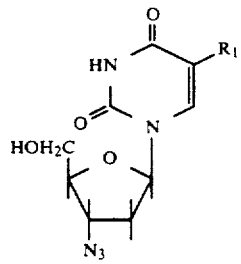

in which:
$R_1$ is H, an alkyl radical or an alkoxy, hydroxyalkyl or halogen radical, from a compound of formula (II)

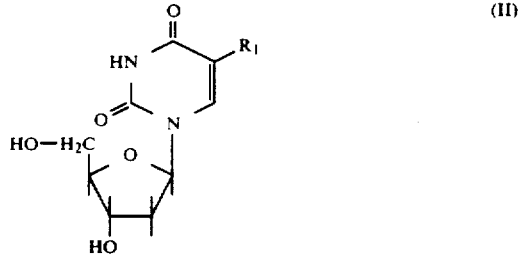

characterized in that the compound of formula II is reacted with a derivative $R_2X$ in which:

X represents a halogen, and $R_2$ a trityl radical, a ($C_{1-3}$ mono- or dialkoxy)trityl radical, a pixyl radical or a radical of the type $(R_3R_4R_5)Si$ where $R_3$, $R_4$ and $R_5$, independently of one another, represent an alkyl group having 1 to 5 carbon atoms or an aryl group, so as to obtain a compound of formula III

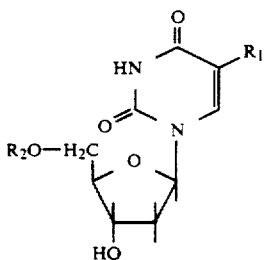
III which is then converted, through the reactants consisting of an azodicarboxylic acid diester and a phosphine or phosphite derivative in a solvent compatible with the reaction conditions, to form a compound of formula IV

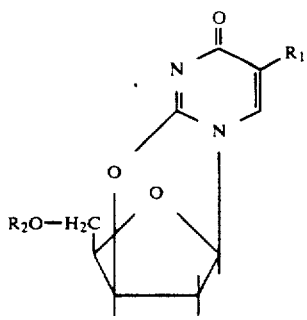
IV which, after an optional separation, is opened in the presence of a metal azide in a solvent compatible with the reaction conditions to lead to a compound of formula V

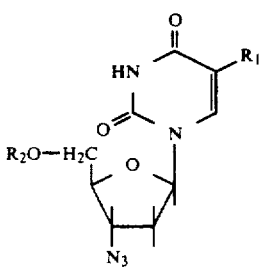
V which, on deprotection of the 5'- function, gives the compound of formula I.

2. Process according to claim 1, characterized in that the derivative $R_2X$ is trityl chloride.

3. Process according to claims 1 or 2, characterized in that the compound of formula IV is prepared directly from the compound of formula III, not isolated or purified, using a compatible solvent and reaction conditions suited to both compounds.

4. Process according to claim 3, characterized in that the solvent is an anhydrous aprotic solvent and in that an organic or inorganic base is combined therewith.

5. Process according to claim 4, characterized in that the solvent is selected from DMF, HMPT and DMSO.

6. Process according to claim 4, characterized in that the base is selected from tertiary amines and alkali metal carbonates.

7. Process according to claim 1 characterized in that the phosphine used is triphenylphosphine.

8. Process according to claim 1 characterized in that the azodicarboxylic acid diester is an alkyl or aryl ester.

9. Process according to claim 8, characterized in that the diester is diisopropyl azodicarboxylate (DIAD) or diethyl azodicarboxylate (DEAD).

10. Process according to claim 1 characterized in that the phosphine or phosphite and the azodicarboxylate diester are used in molar excess relative to the compound of formula III.

11. Process according to claim 1 characterized in that the opening reaction is performed in the presence of an excess of alkali metal azide in a polar solvent.

12. Process according to claim 11, characterized in that this excess is of the order of 1.5 to 15 equivalents per mole of compound of formula IV.

13. Process according to claim 11 characterized in that the polar solvent used is DMF.

14. Process according to claim 1 characterized in that the deprotection of the 5' position of the compound of formula V is carried out using an acidic reagent of the Lewis acid or protic acid type.

15. Process according to claim 14, characterized in that this deprotection is carried out with a reagent selected from boron trifluoride etherate, halogen hydracids and acetic acid in the presence of water.

16. Compound of formula IV, by way of an intermediate in the preparation of a compound of formula I according to claim 1.

17. Process according to claim 6, characterized in that the base is a tertiary amine selected from b 4-dimethylaminopyridine, 1,4-diazabicyclonon-5-ene, 1,4-diazobicyclo-octane, 1,8-diazabicycloundec-7-ene, triethylbutylamine, and tri-n-butylamine.

* * * * *

UNITED STATES PATENT AND TRADEMARK OFFICE
CERTIFICATE OF CORRECTION

PATENT NO. : 5,124,442
DATED : June 23, 1992
INVENTOR(S) : Stanislas Czernecki, et al.

It is certified that error appears in the above-identified patent and that said Letters Patent is hereby corrected as shown below:

This certificate supercedes certificate of correction issued May 8, 2001, the number was erroneoulsy mentioned and should be deleted since no certificate of correction was granted.

Signed and Sealed this

Ninth Day of October, 2001

Attest:

NICHOLAS P. GODICI
*Attesting Officer*  *Acting Director of the United States Patent and Trademark Office*